United States Patent
Bhatt et al.

(10) Patent No.: US 6,187,965 B1
(45) Date of Patent: Feb. 13, 2001

(54) PROCESS FOR RECOVERING HIGH BOILING SOLVENTS FROM A PHOTOLITHOGRAPHIC WASTE STREAM COMPRISING AT LEAST 10 PERCENT BY WEIGHT OF MONOMERIC UNITS

(75) Inventors: Anilkumar C. Bhatt, Johnson City; Jerome J. Wagner, Endicott, both of NY (US)

(73) Assignee: International Business Machines Corporation, Armonk, NY (US)

( * ) Notice: Under 35 U.S.C. 154(b), the term of this patent shall be extended for 0 days.

(21) Appl. No.: 09/188,007

(22) Filed: Nov. 6, 1998

(51) Int. Cl.⁷ .......................... C07C 29/80; C07C 69/96; C07D 317/36; C07D 307/33
(52) U.S. Cl. .......................... 568/810; 549/230; 549/295; 558/260
(58) Field of Search .......................... 568/810; 549/230, 549/295; 558/260

(56) References Cited

U.S. PATENT DOCUMENTS

| | | | |
|---|---|---|---|
| 3,951,769 | 4/1976 | Schlesinger | 204/159.11 |
| 4,187,205 | 2/1980 | Hatano et al. | 280/45.9 D |
| 4,256,774 | 3/1981 | Strobel et al. | 426/428 |
| 4,279,937 | 7/1981 | Strobel et al. | 426/428 |
| 4,413,105 | 11/1983 | Koenig | 525/482 |
| 4,873,174 | 10/1989 | Dhillon et al. | 435/309 |
| 5,066,568 | 11/1991 | Hsieh et al. | 430/325 |
| 5,281,723 | 1/1994 | Bantu et al. | 549/230 |
| 5,296,567 | 3/1994 | Baumann et al. | 526/172 |
| 5,310,428 | 5/1994 | Bhatt et al. | 134/2 |
| 5,411,678 | 5/1995 | Sim | 252/548 |
| 5,427,710 | 6/1995 | Stevens | 252/548 |
| 5,431,739 | 7/1995 | Bengston | 134/2 |
| 5,487,789 | 1/1996 | Sim | 134/38 |

*Primary Examiner*—Ba K. Trinh
(74) *Attorney, Agent, or Firm*—William N. Hogg

(57) ABSTRACT

A method of recovering benzyl alcohol, gamma butyrolactone, or propylene carbonate from an impure effluent stream of an industrial process is provided. The effluent waste stream contains greater than about 10 percent by weight of monomeric units that are reacted to form larger oligomers and polymers. The first step in the recovery process involves polymerizing the monomeric units present in the effluent waste stream under conditions effective to reduce the concentration of monomeric units in the waste stream to less than about 10 weight percent. The waste stream then is fed to a first separation stage where it is separated into (i) a gaseous stream of water, soluble gases, and volatile contaminants and (ii) a suspension comprising the high boiling solvent, semi-volatile materials, and non-volatile contaminants and materials. Then the dewatered, low vapor pressure, high boiling solvent-containing suspension is either distilled or evaporated to separate the high boiling solvent from non-volatile materials. In this second separation stage, the solvent-containing suspension is separated into (i) a solvent-containing fraction, and (ii) a sludge fraction. The sludge fraction contains non-volatile materials in the high boiling solvent.

24 Claims, 3 Drawing Sheets

PROCESS FOR RECOVERING HIGH BOILING SOLVENTS FROM A PHOTOLITHOGRAPHIC WASTE STREAM COMPRISING AT LEAST 10 PERCENT BY WEIGHT OF MONOMERIC UNITS

CROSS-REFERENCE TO RELATED APPLICATIONS

This application is related to application No. 09/188,006 Nov. 06, 1998 entitled "Process For Recovering High Boiling Solvents From A Photlithographic Waste Stream Comprising Less Than 10 Percent By Weight Of Monomeric Units" filed on the same day as the present application.

BACKGROUND

Photolithography plays a critical role in the art of printed circuit packaging. Photolithography is used to define in a thin film of photoresist those regions from which copper is to be selectively etched to subtractively form circuitization, or to which copper is selectively plated to additively form circuitization. Photolithography is also used to personalize soldermasks and dielectric layers.

There are basically two types of photoresist: negative acting and positive acting. Positive photoresists and negative photoresists are both formed from monomers, hereinafter referred to as "monomeric units", such as, for example, acrylates and ethers of bisphenol A. Examples of monomeric units used in the conventional photoresists are as follows: t-butyl acrylate, 1, 5 pentanediol diacrylate, N,N-diethylaminoethyl acrylate, ethylene glycol diacrylate, 1,4-butanediol diacrylate, diethylene glycol diacrylate, hexamethylene glycol diacrylate, 1,3-propanediol diacrylate, decamethylene glycol diacrylate, decamethylene glycol dimethacrylate, 1,4-cyclohexanediol diacrylate, 2,2-dimethylolpropane diacrylate, glycerol diacrylate, tripropylene glycol diacrylate, glycerol triacrylate, trimethylolpropane triacrylate, pentaerythritol triacrylate, polyoxyethylated trimethylolpropane triacrylate and trimethacrylate and similar compounds as disclosed in U.S. Pat. No. 3,380,831, 2,2-di-(p-hydroxyphenyl)-propane diacrylate, pentaerythritol tetraacrylate, 2,2-di(p-hydrohyphenyl)-propane dimethacrylate, triethylene glycol diacrylate, polyoxyethyl-2,2-di(p-hydroxyphenyl)-propane dimethacrylate, di-(3-methacryloxy-2-hydroxypropyl) ether of bisphenol-A, di-(2-methacryloxyethyl) ether of bisphenol-A, di-(3-acryloxy-2-hydroxypropyl) ether of bisphenol-A, di-(2-acryloxyethyl) ether of bisphenol-A, di-(3-methacryloxy-2-hydroxypropyl) ether of tetrachloro-bisphenol-A, di-(2-methacryloxyethyl) ether oftetrachloro-bisphenol-A, di-(3-methacryloxy-2-hydroxypropyl) etheroftetrabromo-bisphenol-A, di-(2-methacryloxyethyl) ether of tetrabromo-bisphenol-A, di-(3-methacryloxy-2-hydroxypropyl) ether of 1,4-butanediol, di-(3-methacryloxy-2-hydroxypropyl) ether of diphenolic acid, triethylene glycol dimethacrylate, polyoxypropyltrimethylol propane triacrylate, ethylene glycol dimethacrylate, butylene glycol dimethacrylate, 1,3-propanediol dimethacrylate, 1,2,4-butanetriol trimethacrylate, 2,2,4-trimethyl-1,3-pentanediol dimethacrylate, pentaerythritol trimethacrylate, 1-phenyl ethylene-1,2-dimethacrylate, pentaerythritol tetramethacrylate, trimethylol propane trimethacrylate, 1,5-pentanediol dimethacrylate, diallyl fumarate, styrene, 1,4-benzenediol dimethacrylate, 1,4-diisopropenyl benzene, and 1,3,5-triisopropenyl benzene.

In addition to the reactive monomeric units mentioned above, the photoimageable compositions used to form negative and positive photoresists can also contain one or more free radical-initiated and polymerizable species with molecular weight of at least about 300. Monomeric units of this type are an alkylene or a polyalkylene glycol diacrylate and those described in U.S. Pat. No. 2,927,022. Particulate thickeners such as, for example, silicas, clays, alumina, bentonites, kalonites, and the like can also be used in the photoimageable compositions. Dyes and pigments may also be added to increase the visibility of the resist image. Any colorant used however, should be transparent to the actinic radiation used to polymerize the monomeric units. With some compositions, it is desirable to add a plasticizer, either solid or liquid, to give flexibility to the film or coating. Generally inert solvents which are volatile at ordinary pressures are used to prepare these photoresist compositions.

Photoimageable compositions are also used to form soldermasks. Such compositions typically comprise acrylate monomers or epoxy monomers, free radical initiators, and thermal cross-linking agents. A photoimageable soldermask composition which contains acrylate monomers and a free radical initiator is described in U.S. Pat. No. 5,026,624 assigned to the assignee of the present application, disclosure of which is incorporated herein by reference. A photoimageable soldermask composition, which contains cationically polymerizable epoxy monomers and cationic photoinitiators, is described in U.S. Pat. No. 5,300,402.

During processing of the photoresist or soldermask, an acrylate-based or epoxy-based photoimageable film is first applied to a circuit board and then patterned by exposure of preselected regions to actinic radiation. To develop the resulting pattern of polymerized and unpolymerized material, the coated board is contacted with a liquid developer either by dipping or spraying. The commonly assigned U.S. Pat. No. 5,268,260 of N. R. Bantu, Anilkumar Bhatt, Ashwinkumar Bhatt, G. W. Jones, J. A. Kotylo, R. F. Owen, K. I. Papathomas, and A. K. Vardya for Photoresist Develop and Strip Solvent Compositions and Method for Their Use, incorporated herein by reference, describes the use of the low vapor pressure, high boiling solvents benzyl alcohol, gamma butyrolactone, and propylene carbonate for developing acrylate-based photoresist such as DuPont Riston T-168 and solvent-processable soldermasks such as the Vacrel 700 and 900 series. In the case of negative acting photoresists, the unpolymerized material used to form the photoresist, i.e., the monomeric units of acrylate or epoxy, is dissolved in the developer at low temperature, preferably between 15° C. and 45° C. Developing of the soldermask involves the same steps except that the unpolymerized material is dissolved in the developer at a temperature of from about 15° C. to about 80° C. Positive acting resists behave oppositely. Actinic radiation renders the positive acting photoresist more soluble in the developer, and the exposed regions are removed preferentially by the developer.

The dissolved material, which consists primarily of monomeric units of the acrylate or epoxy, and the developing solution are then removed from the board by allowing the solution to run off into a containment tank. To further enhance development of the pattern, the residual dissolved materials and developing solution are rinsed from the board, preferably with warm water. High vapor pressure organic solvents, such as isopropyl alcohol, acetone, methyl ethyl ketone and xylene, may also be used as a rinse. The effluent produced by this process is an impure solution of developer, which is laden with monomeric units and other impurities. Typically, the effluent contains greater than 10 percent by weight of monomeric units.

Large volumes of liquid waste containing impure benzyl alcohol, impure propylene carbonate, or impure gamma butyrolactone result from the above-described developing process. This liquid waste must be further processed prior to release into the environment (as by incineration). Such methods of dealing with the liquid waste are costly. Moreover, the costs to the industry in terms of purchasing virgin material, i.e., pure benzyl alcohol, pure gamma butyrolactone, and pure propylene carbonate and the costs to the environment of manufacturing virgin material are significant.

Accordingly, it is desirable to have a new method of reducing the amount of solvent containing waste that results from this and other industrial processes. A method that permits recovery of relatively pure solvent which can then be re-used by the industry, and thus prevent the need to purchase virgin material, is especially desirable.

SUMMARY OF THE INVENTION

In accordance with the present invention, a method of recovering benzyl alcohol, gamma butyrolactone, or propylene carbonate from an impure effluent stream of an industrial process is provided. The effluent waste stream contains greater than about 10 percent by weight of monomeric units that are reacted to form larger oligomers and polymers. Typically, the effluent waste stream also contains the oxidation, hydrolysis, and/or other decomposition products of one of the high boiling solvents. Thus, an effluent stream which contains benzyl alcohol, typically, also contains benzoic acid and/or benzaldehyde. An industrial processing effluent stream which contains gamma butyrolactone, typically, also contains and gamma-butyric acid and/or hydroxybutyric acid. An industrial processing effluent stream which contains propylene carbonate, typically, also contains propylene glycol, propylene oxide and carbon dioxide. Such effluent streams are produced when benzyl alcohol, gamma butyrolactone, or propylene carbonate is used as a developer in a photolithographic process.

The first step in the recovery process involves polymerizing the monomeric units present in the effluent waste stream under conditions effective to reduce the concentration of monomeric units in the waste stream to less than about 10 weight percent. The waste stream then is fed to a first separation stage where it is separated into (i) a gaseous stream of water, soluble gases, and volatile contaminants and (ii) a suspension comprising the high boiling solvent, semi-volatile materials, and non-volatile contaminants and materials. This first separation stage lowers the concentration of water in the suspension to a level that is low enough to substantially avoid further hydrolysis of the low vapor pressure, high boiling solvent in the suspension. Then the dewatered low vapor pressure, high boiling solvent-containing suspension is either distilled or evaporated, for example in a wiped film type evaporator, to separate the high boiling solvent from non-volatile materials. In this second separation stage, the solvent-containing suspension is separated into (i) a solvent-containing fraction, and (ii) a sludge fraction. The sludge fraction contains non-volatile materials in the high boiling solvent.

DETAILED DESCRIPTION OF THE INVENTION

Industrial processes which employ relatively pure benzyl alcohol, propylene carbonate or gamma butyrolactone as a developer to remove unpolymerized material from a photo-processed photoresist or solder mask film result in the production of an impure benzyl alcohol effluent, an impure propylene carbonate effluent, or an impure gamma butyrolactone effluent, respectively. Such effluents typically contain (i) above about 50 weight percent of the high boiling solvent, and generally from about 85 weight percent to about 97 weight percent of the high boiling solvent, (ii) up to about 20 weight percent or more monomers, and generally from about 10 weight percent to about 15 weight percent of monomeric units, (iii) up to about 5 weight percent, and generally from about 0.05 weight percent to about 1 weight percent decomposition products of the high boiling solvent, (iv) up to about 10 weight percent of other components of the photoimageable compositions, such as, for example, plasticizers, dyes, initiators, thickeners, initiators, or thermal curing agents, hereinafter referred to as "materials", and (v) up to about 20 weight percent, and generally from about 0.05 weight percent to about 5 weight percent of water. These weight percentages should total 100 weight percent but may total less than 100 weight percent if other impurities are present.

While the invention is described and illustrated with respect to recovery of benzyl alcohol, gamma butyrolactone, and propylene carbonate from a waste stream, it is, of course, to be understood that the method can also be applied to other aromatic alcohols, such as for example 1-benzyl benzyl alcohol, benzyl tertiary butanol, 2 benzyloxy ethanol, 5-phenyl-1 pentanol, phenyl ethyl alcohol, 3-(n-benzyl-n-methyl amino)-1-propanol. The optimum temperatures and pressures for recovery of these aromatic alcohols via the present method are easily determined and within the ordinary skill of the art.

In order to recycle the low vapor pressure, high boiling solvent for reuse as a developing agent or stripping agent, it is necessary to recover a purified solvent. By purified solvent is generally meant a solvent that is typically 99 or greater weight percent pure; that is essentially free of monomeric units and materials; and that contains less than about 0.1 weight percent water, and preferably less than about 0.05 weight percent water, and less than 0.01 weight percent of the decomposition products of the solvent, as assayed by gas chromatography.

Figure 1:
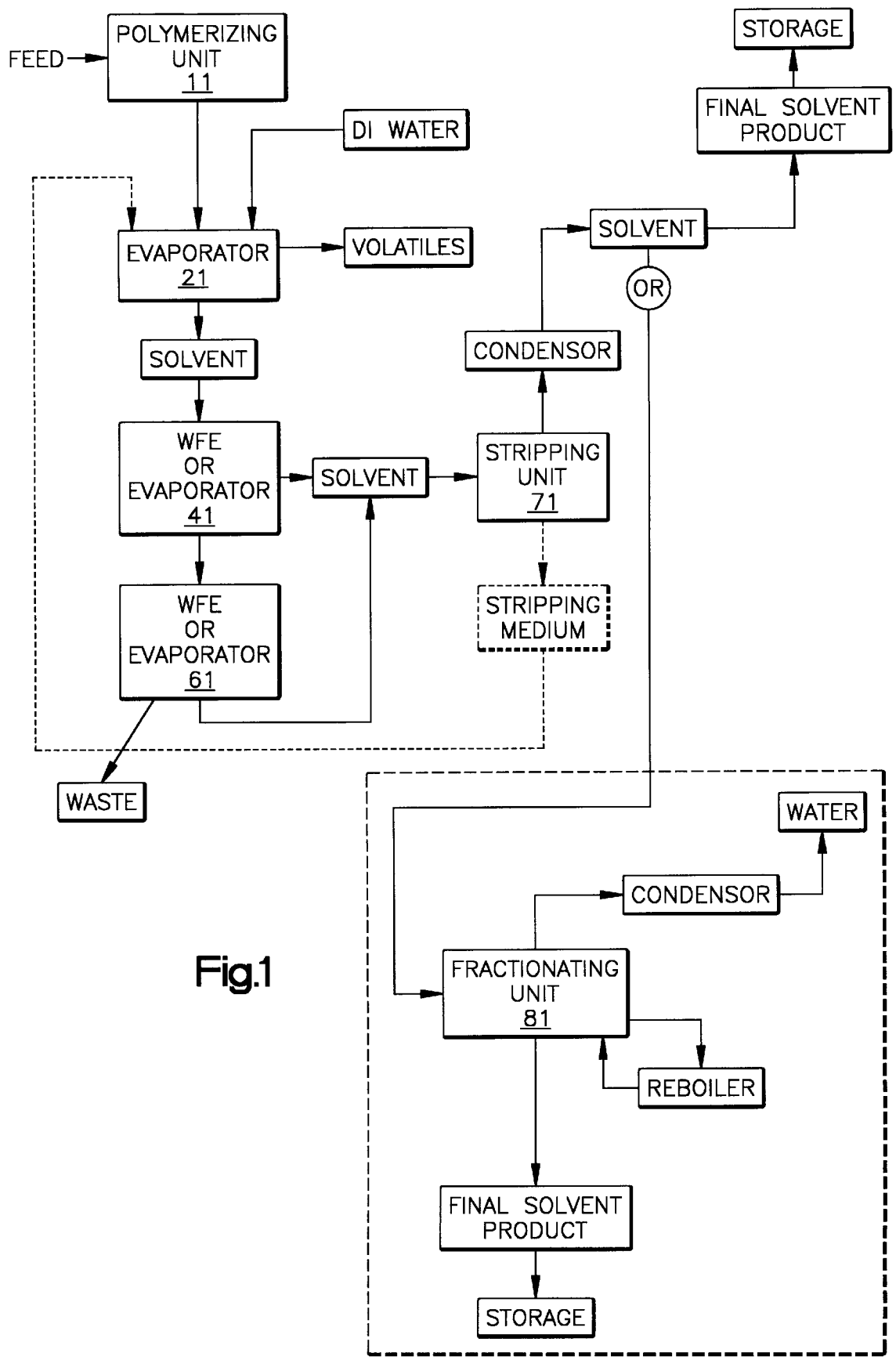
FIG. 1 is a flow chart which generally exemplifies a process for recovering a low vapor pressure, high boiling solvent from a waste stream comprising greater than about 10 weight percent of monomeric units, such as acrylates.

FIG. 1 is a flow chart which exemplifies a process for recovering the low vapor pressure, high boiling solvent from an effluent stream of a process in which such solvent is used as a developing agent. This effluent stream comprises the solvent, water, monomeric units such as acrylate, acrylate esters, or the epoxy intermediate bisphenol A, decomposition products of the solvent, and other materials. The effluent stream comprises at least about 10 weight percent of the monomeric units and may contain up to about 20 weight percent of the monomeric units.

Figure 2A:
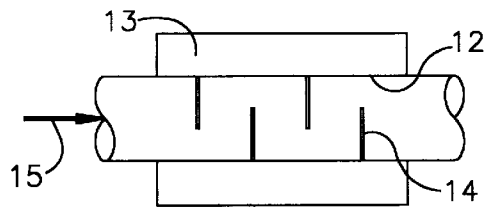
FIG. 2 is a schematic representation of a polymerization unit useful in reducing the concentration of monomeric units present in the effluent waste stream.
Figure 2B:
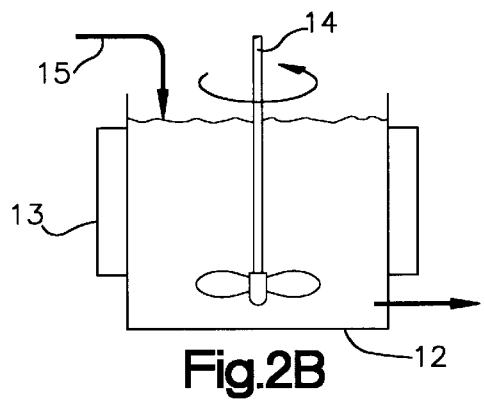

In the recovery process illustrated in FIG. 1, the first step involves feeding the waste stream to a polymerization unit and then polymerizing a substantial portion of the monomeric units in the effluent stream. Polymerization is accomplished by heating or, preferably, by exposing the effluent stream to actinic radiation for a time sufficient to reduce the concentration of monomeric units in the stream to less than about 5 weight percent. Preferably, as shown in FIG. 2, the polymerization unit is a glass tube which is transmissive to actinic radiation. The waste stream that is released from the polymerization step contains (i) from about 85 weight percent to about 97 weight percent of the solvent, (ii) less than 10 weight percent monomeric units, generally from about 1 weight percent to about 5 weight percent monomeric units, (iii) from about 10 weight percent to about 25 weight percent of "polymerization product," (iv) from about 0.05 weight percent to about 1 weight percent of the decomposition product of the solvent, and (v) from about 0.05 weight percent to about 5 weight percent of water. The "polymerization product" is a mixture of polymers of varying lengths, including small polymers which tend to be soluble, non-filterable, non-settleable, and fluid-like, and larger polymers which tend to be insoluble, discrete solid particles. In some instances the polymerization product is a unfilterable gelatinous mass. Optionally, chemically compatible materials such as, for example, diatomaceous earth, are added to the polymerization product as needed to enhance its filterability. Alternatively, polymerization can be inhibited throught the addition of quinone-type stabilizers.

Figure 3:
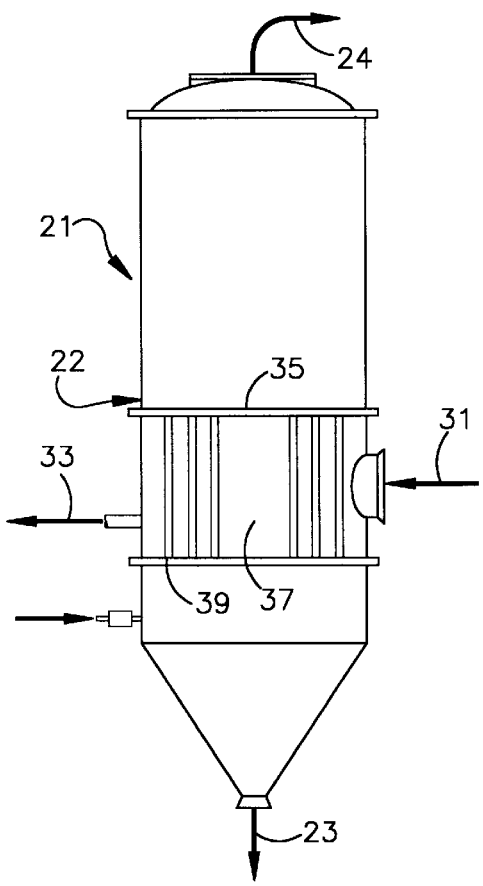
FIG. 3 is a cutaway view of a single stage, vertical tube heat exchanger type evaporator useful in separating the solvent from water and volatiles.

Thereafter, the effluent stream is fed to dewatering unit, which is the first separation stage. In the first separation stage the effluent stream is separated into two streams (i) a gaseous stream of water and volatiles withdrawn at the top of evaporator 21, and (ii) a liquid stream containing the high boiling solvent at the bottom of evaporator 21. The dewatering unit may be a short tube, vertical pipe heat exchanger type evaporator 21, as shown in FIG. 3. Alternatively, the first stage separator may be a boiling pot, flash evaporator, or any other type of heater which allows for removal of the water-bearing vapor stream from the liquid solvent-containing stream.

This first separation stage lowers the concentration of water in the liquid stream to a level that is low enough to substantially avoid hydrolysis of the low vapor pressure, high boiling solvent to the corresponding decomposition product. In the first stage separator, as heat exchanger type evaporator 21, the total pressure is maintained higher than the vapor pressure of the solvent at its open cup flash point. The temperature of the process stream is maintained at a temperature below the flash cup point of the solvent. Accordingly, in the first stage separator, the effluent stream which comprises benzyl alcohol is maintained at a temperature of from about 80° C. to about 90° C., and the total pressure in evaporator 21 is maintained at corresponding levels of from about 15 torr to about 25 torr. When the effluent stream comprises gamma butyrolactone, the temperature of the waste stream is maintained at about 75° C. to about 85° C. and the total pressure in evaporator 21 is maintained at corresponding levels of about 20 torr to about 35 torr. When the effluent stream comprises propylene carbonate, the temperature of the waste stream is maintained at about 115° C. to about 125° C. and the total pressure in evaporator 21 is maintained at corresponding levels of about 25 torr to about 35 torr.

The bottom product of the first separation stage is a dewatered solvent containing (i) from about 90 weight percent to about 98 weight percent of the respective solvent, (ii) from about 10 weight percent to about 25 weight percent of polymerization products and other materials, (iii) from about 0.03 weight percent to about 1 weight percent of the decomposition product of the solvent, and (iv) from about 0.03 weight percent to about 0.1 weight percent of water.

The dewatered solvent from the first stage separation is then distilled or evaporated, preferably in a wiped film type evaporator 41, to separate the solvent from non-volatile contaminants. When the dewatered solvent comprises benzyl alcohol, the pressure in the evaporator 41 is maintained below about 15 torr, for example from about 5 to about 11 torr and the temperature is maintained at corresponding values of from about 81° C. to about 95° C. When the dewatered solvent comprises propylene carbonate, the pressure in evaporator 41 is maintained below about below about 30 torr, for example from about 6 to about 22 torr and the temperature is maintained at corresponding values of from about 116° C. to about 127° C. When the dewatered solvent comprises gamma butyrolactone, the pressure in evaporator 41 is maintained below about 25 torr, for example from about 8 to about 20 torr and the temperature is maintained at corresponding values of from about 76° C. to about 93° C. In this stage dewatered solvent is separated into a solvent-containing vapor fraction, and a sludge fraction. The sludge fraction, i.e. the bottom product, contains inert contaminants, such as fillers, and non-volatile contaminants, such as benzoic acid, in the corresponding solvent. The solvent-containing vapor fraction from this second stage separation, i.e., overhead product, is from about 95 to about 99 weight percent solvent.

Figures 5, 6:
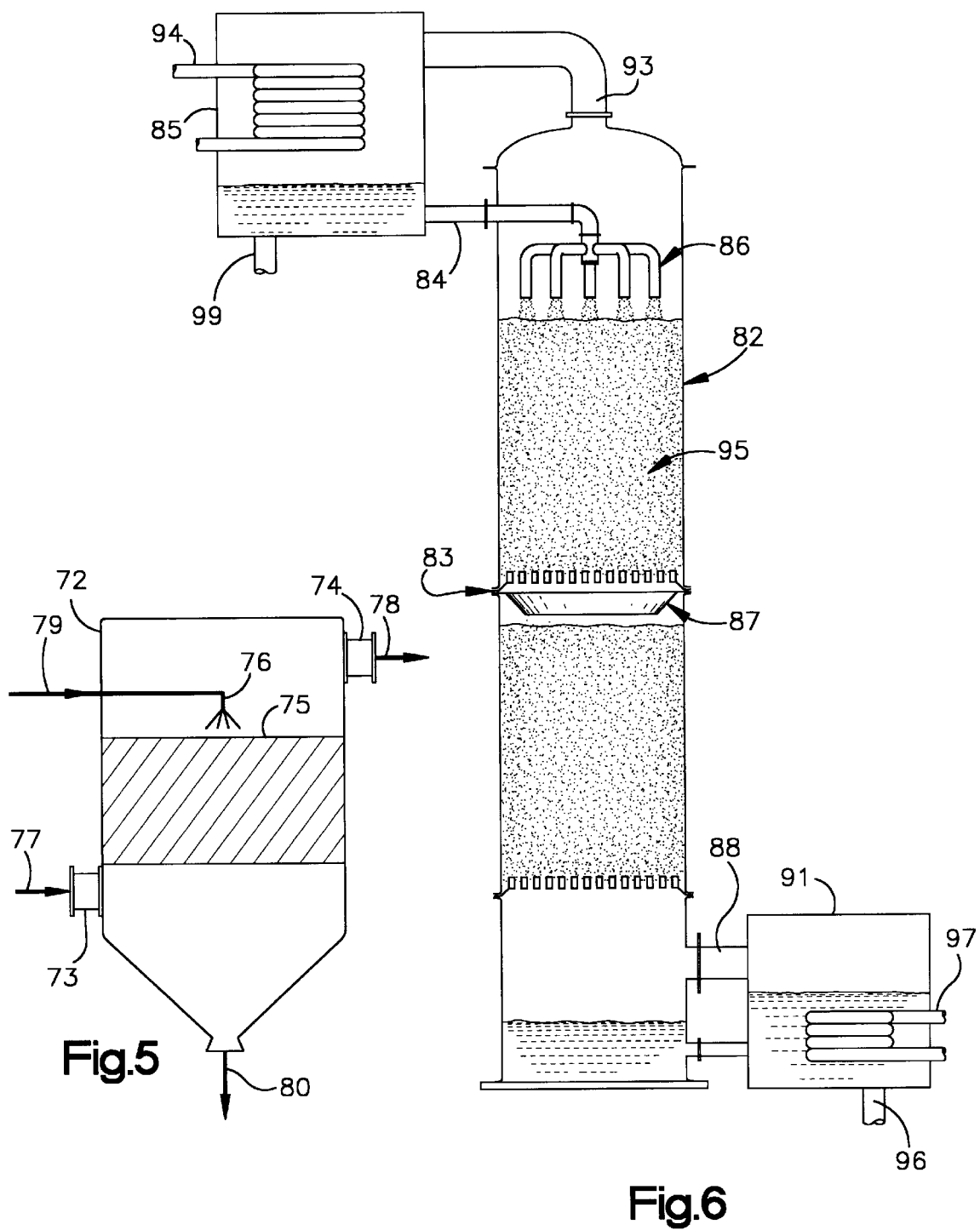
FIG. 5 is a schematic representation of a stripping unit useful in separation of the solvent from semi-volatile materials.
FIG. 6 is a cutaway view of a packed tower distillation column useful in separation of the solvent from the decomposition product of the solvent and other high vapor pressure contaminants.

Preferably, the overhead product, i.e., the dewatered, evaporated solvent-containing vapor fraction is fed to stripping unit 71, which may be a packed mass transfer unit 71, as shown in FIG. 5. In stripping unit 71 semi-volatile contaminants, such as plasticizers and any remaining monomeric units, are removed from the vapor using a cool, compatible, liquid solvent, as a mass transfer medium. As used herein, "cool" means that the temperature of the mass transfer medium is at least about 20° C. less than the temperature of the vapor. Preferably, the temperature of the mass transfer medium is between about 35° C. to about 70° C. Preferably, the ratio of the mass transfer medium to vapor mass is about 1:7.

In stripping unit 71, heat from the vaporized semi-volatile contaminants is transferred to the mass transfer medium. Such transfer causes the semi-volatile contaminants to condense to liquid, which results in their removal from the vapor stream. Concurrently, a small amount of the mass transfer medium is vaporized and enters the product stream. Accordingly, to avoid introduction of other contaminants into the vapor fraction, it is preferred that a relatively pure benzyl alcohol be used as the mass transfer medium when benzyl alcohol is the primary solvent in the waste stream.

The top product of this stage is a solvent-containing vapor which is subsequently condensed into a stripped solvent fraction containing greater than about 96 weight percent solvent. The bottom product is a liquid containing the mass transfer medium and the semi-volatile species. In those cases where the mass transfer medium employed is the same as the solvent being recovered, it is preferred that the bottom product be fed back to the first stage evaporator 21 to increase recovery of the respective solvent.

Depending upon purity requirements, the stripped solvent fraction may either be stored for future use or further purified. Further purification is accomplished by feeding the stripped solvent-containing fraction to a fractionating unit 81, which may be a packed tower of the type shown in FIG. 6. In fractionating unit 81, the stripped solvent containing fraction is separated into a higher vapor pressure, lower boiling point top product (fractionation waste) and a lower vapor pressure, higher boiling point bottom product, hereinafter referred to as the "final solvent product". Preferably a reboiler heats fluid which is collected from and recycled back into the bottom of fractionating unit 81. A cool condensate is introduced into the top of fractionating unit 81.

In those instances where the stripped solvent containing fraction comprises benzyl alcohol, it is preferred that the top pressure of fractionating unit 81 be less than about 10 torr, and generally from about 1 to about 4 torr, and the bottom pressure be less than about 25 torr, and generally from about 10 to about 20 torr. The top product of such process is benzaldehyde and the bottom product is benzyl alcohol that is about 99 or greater weight percent pure. In those instances where the stripped solvent containing fraction comprises propylene carbonate, it is preferred that the top pressure of the fractionating unit be less than about 15 torr, and generally from about 4 torr to about 10 torr, and the bottom pressure be less than about 25 torr, and generally from about 15 to about 20 torr. The top product of such process is water and propylene glycol and the bottom product is propylene carbonate that is about 99 or greater weight percent pure. In those instances where the stripped solvent containing fraction comprises gamma butyrolactone, it is preferred that the top pressure of the fractionating unit be less than about 10 torr, and generally from about 2 torr to about 5 torr, and the bottom pressure be less than about 25 torr and generally is from about 15 torr to about 20 torr. The top product of such process is water and hydrobutyric acid and the bottom product is gamma butyrolactone that is about 99 or greater weight percent pure.

The product of fractionating unit 81, i.e., the final solvent product, is about 99 or greater weight percent solvent and is essentially free of materials, photoresist products, and other solids. The final solvent product is also essentially free of water and decomposition products of the solvent, containing less than about 0.03 weight percent water and less than about 0.01 weight percent of the decomposition products.

Optionally, the low vapor pressure, high boiling solvent may also be recovered from the bottom product of evaporator 41, i.e., from the sludge fraction. The bottom product contains inert contaminants, such as fillers, and non-volatile contaminants, such as benzoic acid, in the corresponding solvent. The bottom product contains from about 70 to about 95 weight percent solvent, balance solids. In this optional step, the bottom product of the evaporator 41 is fed to a further evaporator 61. The overhead product of the second evaporator goes to stripper 71 as shown in FIG. 1. The bottom product of the evaporator unit 61 is a polymer rich material that is discharged and collected in storage tanks or drums. If the collected waste product contains greater than about 20 weight percent reactive monomer, it is preferred that from about 5 ppm to about 500 ppm of an antioxidant or stabilizer be added to the collected waste product. Exemplary stabilizers are quinone type stabilizers, such as hydroquinone, p-methoxy phenol, alkyl substituted hydroquinones, aryl substituted quinones, tert-butyl catechol, pyrogallol, naphthylamines, beta-napthol, 2,6-di-tert-butyl-p-cresol, phenothiazine, pyridine, nitrobenzene, dinitrobenzene, p-toluene quinone, hydroquinone monomethyl ether, as well as copper organo-metallics.

Optionally, to reduce combustion potential all process steps are conducted under a nitrogen blanket. The use of a nitrogen blanket also provides a higher quality product. Alternatively, from about 5 ppm to about 500 ppm of stabilizer is added to the waste stream prior to processing in evaporator 21, prior to processing in evaporator 41, or prior to waste shipment. Addition of the stabilizer prevents exothermic reactions from occurring during the various processing steps and waste shipment and storage. The addition of such stabilizer is especially desirable when the respective waste stream or waste product contains greater than about 20 weight percent reactive monomer.

Turning now to the individual process steps, the first step of the process in which the effluent waste stream contains at least 10 weight percent of monomeric units is the polymerization of the monomeric units. As shown in FIG. 2, the polymerization reaction is carried out in polymerization unit 11, which comprises a container 12 which is transmissive to actinic radiation, i.e., ultraviolet light of a specific output wavelength. Container 12 is attached or adjacent to actinic radiation source 13.

Waste stream 15 enters container 12 of polymerization unit 11 where it is exposed to actinic radiation from actinic radiation source 13 for a time and at a temperature sufficient to cause cross-linking of the monomeric units and to reduce the concentration of the monomeric units in waste stream 15 to less than 10 percent by weight. For waste streams containing acrylate monomers, the preferred wavelength is about 365 nm; for epoxy monomers the preferred wavelength is about 1000 nm. The temperature in container 12 is maintained from about 20° C. to about 100° C. Time of exposure of waste stream 15 to the actinic radiation is from about 5 minutes to greater than 24 hours depending on the concentration of monomer in the stream, the composition and fluid characteristics of the stream, the presence of interfering species such as dyes, temperature employed, rate of UV addition, and fouling of the transmissive surface of container 12. The effluent which leaves polymerization unit 11 comprises less than 10 weight percent monomeric units and from about 10 weight percent to about 25 weight percent polymerization products.

Thereafter, the effluent is fed to a dewatering unit 21, which is shown in FIG. 3 as being a short tube vertical heat exchanger type evaporator 21, such as a falling film type evaporator. The short tube vertical heat exchanger type evaporator 21 has a feed stream 22, which is separated in the evaporator 21 into a bottom or liquid stream 23 and an overhead or gas stream 24. Additionally, water, for example, deionized water, may be fed to the top of the evaporator. Heat transferred to this water from the gas stream aids in condensing the solvent vapor, i.e., the benzyl alcohol, gamma butyrolactone, or propylene carbonate in the gas stream, and thereby reduces the loss of the desired solvent with the overhead 24.

Steam enters the heat exchanger type evaporator 21 through steam inlet 31, which is the inlet to a shell and tube type heat exchanger 21. The steam is the shell side medium. In one exemplification the tubes 39 are vapor risers. Evaporating feed rises through the tubes or vapor risers 39. Steam condensate exits the shell and tube heat exchanger 31 through outlet 33.

The total pressure in vertical heat exchanger type evaporator 21 is maintained higher than the vapor pressure of the solvent at its open cup flash point. The temperature of feed stream 22 is raised to a temperature which is approximately 2 to 10° C. below the open flash cup point of the solvent, thereby flashing water and other volatile species and gases from the liquid stream. Accordingly, in the first stage separator, the effluent stream which comprises benzyl alcohol is maintained at a temperature of from about 80° C. to about 90° C., and the total pressure is maintained at from about 15 to about 25 torr. When the effluent stream comprises gamma butyrolactone, the temperature of the waste stream is maintained at about 75° C. to about 85° C. and the total pressure in evaporator 21 is maintained at about 20 torr to about 30 torr. When the effluent stream comprises propylene carbonate, the temperature of the waste stream is maintained at about 115° C. to about 125° C. and the total pressure in evaporator 21 is maintained at about 25 torr to about 35 torr.

Figure 4:
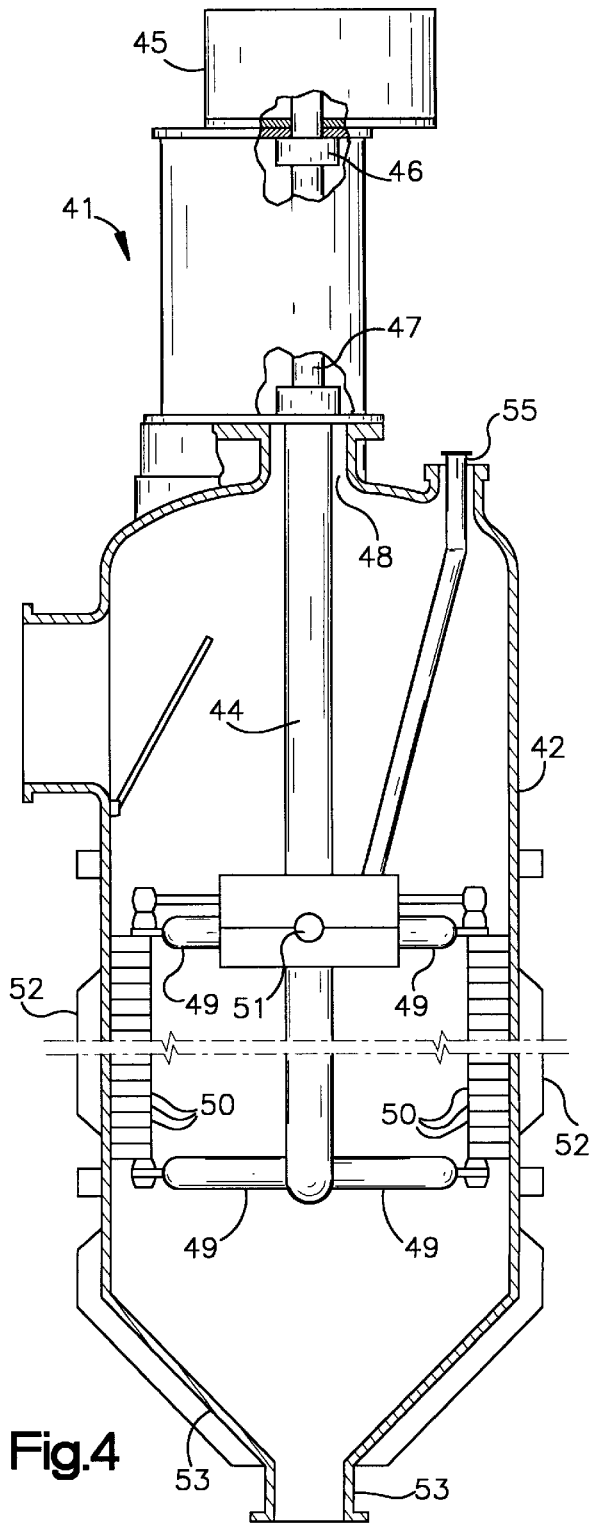
FIG. 4 is a cutaway view of a wiped film evaporator useful in separation of the solvent from non-volatile materials and contaminants.

The liquid product 23 of the first stage separation 21 is then fed to the second stage separation 41. The second stage separator 41 is illustrated in FIG. 4 as a single-effect wiped film evaporator.

A wiped film evaporator 41 has a cylindrical vessel, 42, as a steel vessel. The interior walls of the vessel may be metal, as stainless steel, super alloys, and the like. Alternatively, the interior walls may be lined, for example, with glass or an enamel. By an enamel is meant a porcelain enamel. Porcelain enamels are vitreous or partially devitrified inorganic materials. The glass or enamel lining is bonded to the steel vessel 42.

Wiped film evaporators 41 are characterized by a rotating wiper assembly 43 extending along the vertical axis of the evaporator 41. The rotating wiper assembly 43 includes a rotating shaft 44, arms 49 extending outwardly from the rotating shaft 44, and blades 50 at the ends of the arms 49 for spreading the solvent solution onto the interior wall of the vessel 42.

The rotating shaft 44 is driven by a motor 45, through bearings 46, and coupling 47, extending through a seal 48 in the top of the vessel. The walls of the wiped film evaporator 41 are heated by steam in steam jackets 52.

In operation, the dewatered solvent of the first stage evaporator 21 is introduced into the wiped film evaporator 41 through opening 55. The liquid feed is led to a distributor 51. Centrifugal force and gravity drive the solvent out of the distributor 51 to the blades 50 at the ends of the arms 49. The blades 50 spread the solvent onto the interior surface of the vessel 42, where the steam in the steam jacket 52 heats the solvent giving off a solvent vapor 57. The liquid residues fall to a conical collecting region 53 and outlet 54.

The liquid product of the second stage separation 41 may be further processed, for example through use of a downstream evaporator 61, to concentrate the resist solids and increase solvent distillate yield. The final residue of the downstream evaporator 61 becomes a principal waste of the process. Optionally, a quinone type stabilizer is added to this liquid product to limit exothermic polymerization reactions.

Vapors from units 41 and 61, being solvent substantially free of photoresist materials but containing minor amounts of other volatiles and semi-volatiles such as plasticizers and monomeric units, are fed to a stripping unit 71 where components that are less volatile than the solvent are transferred to a mass transfer medium. The temperature of mass transfer medium is at least about 20° C. lower than temperature of vapor and, preferably, from about 35° C. to about 70° C. The operating pressure within stripping unit 71 varies from a lower pressure at the top where the stripped solvent vapor exits stripping unit 71 to a slightly higher pressure at the bottom where the vapor stream from evaporator 41 enters stripping unit 71.

When the solvent is benzyl alcohol, the pressure in the vapor inlet of the stripping unit is maintained below about 15 torr, for example from about 5 to about 11 torr. When the solvent is propylene carbonate, the pressure in the vapor inlet of the stripping unit is maintained below about 30 torr, for example from about 12 torr to about 22 torr. When the solvent is gamma butyrolactone, the pressure in the vapor inlet of the stripping unit is maintained below about 25 torr, for example from about 8 torr to about 20 torr.

Vapors 77 from units 41 and 61 enter the vapor stripper unit 71 through the vapor inlet connection 73 which, typically, is positioned near the bottom of the equipment shell 72. The vapor flows upward through mass transfer contact means 75, which may be of random packing style, structured packing style, bubble tray style, or any other style which permits thorough contacting of vapor with the liquid stripping media. While flowing through mass transfer contact means 75, the vapor stream is contacted with downward-flowing, cool, clean liquid mass transfer medium 79, which has been distributed over contact means 75 by liquid distributor 76. While flowing through contact means 75, the vapor is stripped of semi-volatile components. Stripped vapor 78 exits the shell of equipment through vapor outlet 74, which, typically, is located near the top of shell 72. The exiting liquid stripping stream 80, which contains semi-volatile species, leaves shell 72 from the bottom of the unit. Movement of the vapor in vapor stripper 71 is caused by pressure differences in the equipment as shown in FIG. 1, with the vapor moving from the higher pressure evaporators 21 and 41 towards the lower pressure condenser. Movement of the liquid stripping media in the vapor stripper 71 is caused by gravity.

Mass transfer medium 79 must be compatible liquid which is non-reactive with the vapor chemistry. Mass transfer medium 79 is selected such that the semi-volatile species are soluble in mass transfer medium 79 at the concentrations and under the conditions which exist in vapor stripping unit 71 during processing of the vapor stream.

Solvent vapors from stripping unit 71 are then condensed into a stripped liquid solvent product that may be stored for future use. Optionally, a portion of the stripped liquid solvent is recycled back to stripping unit 71 for use as mass transfer medium 79.

If desired, the stripped liquid solvent product is introduced into a fractionation column 81 for further purification. In the fractionation column 81, components that are more volatile than the solvent form a vapor phase which is removed from the top of the column and then condensed. The components in the vapor phase include water and decomposition products of the solvent which is being recovered. Examples of decomposition products of the high boiling solvents are benzaldehyde, hydroxybutyric acid, gamma butyric acid, propylene glycol, and propylene oxide.

Fractionation occurs within this unit, with more volatile species traveling to the top of column 81 to be condensed and the less volatile solvent circulating within the bottom of the column 81 as a liquid cooler than its boiling point. Normal methods of distillation column operation, including control of overhead reflux ratio and of bottom reboil ratio, are applied. Condensation is effected by a reflux stream introduced at the top of the column 81. A liquid stream comprising solvent leaves the bottom of column 81. This stream may be removed from the system and stored as the final solvent product. Alternatively, the liquid stream may be introduced into a re-boiler, which heats the liquid and revaporizes more volatile contaminants. The vapor product from the reboiler is re-introduced into the fractionation column for further purification.

In instances where the stripped solvent is benzyl alcohol, the operating pressure within the column 81 varies from about 1 to about 4 Torr at the top to about 10 to about 20 Torr at the bottom. In instances where the stripped solvent is gamma butyrolactone, the operating pressure within the column 81 varies from about 2 to about 5 Torr at the top to about 15 to about 20 Torr at the bottom. In instances where the stripped solvent is propylene carbonate, the operating pressure within the column 81 varies from about 4 to about 10 Torr at the top to about 15 to about 20 Torr at the bottom.

Details of a packed tower distillation column 81 are shown in FIG. 6. Structurally, the packed tower 81 includes a shell or body 82, with a condenser 85 at the top and a reboiler 91 at the bottom. Feed is introduced into the tower 81 through liquid feed means 83, to a liquid distributor similar to 86, and a packing restrainer 87; the feed location may be at about one-half the tower's height. The liquid distributor 86 and the packing restrainer 87 distribute the feed and the condenser return 84 onto and through the packing 95.

Upward flowing gas, for example, return 88 from the reboiler 91, contacts the downward flowing liquid, providing a low boiling, high vapor pressure top product 93 at the condenser 85, which is condensed by a condenser heat exchanger 94 and recovered as a high vapor pressure, low boiling temperature liquid 99, and a high boiling, low vapor pressure product at the reboiler 91, which is recovered as a liquid product 96. The remaining reboiler liquid is vaporized by heat exchanger 97. A final solvent product, suitable for re-use in manufacturing, is discharged from the bottom of the fractionation column 81 or from liquid product 96.

While the invention has been described with respect to certain preferred embodiments and exemplifications, the invention may also be used to purify solvents from other industrial processes. Accordingly, the methods described herein may also be used to purify the low vapor pressure, high boiling solvents from waste streams comprising ionic materials and contaminants, color bodies, polymers, oils, paints, carbon, and resins as well as photoresist products. It is not intended to limit the scope of the invention to the preferred embodiments and exemplifications, but solely by the claims appended hereto.

What is claimed is:

1. A method of recovering a low vapor pressure, high boiling solvent from an effluent stream comprising said solvent, water, and at least 10 weight percent of monomeric units, said method comprising the steps of:
    (a) polymerizing the monomeric units in the effluent stream under conditions effective to reduce the monomeric units to less than 10 weight percent of the stream;
    (b) feeding the effluent stream into a first stage separator and separating water and volatiles from the effluent stream to provide a dewatered solvent fraction; and
    (c) feeding the dewatered solvent fraction into a second stage separator and separating said dewatered fraction into a vapor fraction containing said solvent and a sludge fraction containing non-volatile materials.

2. The method of claim 1 wherein the solvent is selected from the group consisting of benzyl alcohol, gamma butyrolactone, and propylene carbonate.

3. The method of claim 1 further comprising the step of stripping semi-volatile species from said vapor fraction to provide a stripped liquid solvent.

4. The method of claim 3 further comprising the step of separating the stripped liquid solvent into a higher vapor pressure fraction comprising substances more volatile than said solvent and a lower vapor pressure fraction comprising said solvent.

5. The method of claim 1 further comprising the step of separating the vapor fraction into a higher vapor pressure fraction comprising substances more volatile than said solvent and a lower vapor pressure fraction comprising said solvent.

6. The method of claim 1 wherein polymerization step (a) is accomplished by exposing the effluent stream to actinic radiation.

7. The method of claim 1 wherein the temperature is maintained below the open cup flash point of the solvent.

8. The method of claim 1 wherein said solvent is benzyl alcohol and the pressure in said first stage separator is maintained below about 25 torr.

9. The method of claim 1 wherein the solvent is an aromatic alcohol.

10. The method of claim 1 wherein the first stage separator is a heat exchanger type evaporator.

11. The method of claim 1 wherein the second stage separator is a wiped film evaporator.

12. The method of claim 1 wherein one or more of steps (a), (b), and (c) are performed under a nitrogen blanket.

13. The method of claim 1 wherein from about 5 ppm to about 500 ppm of a stabilizer is added to the waste stream prior to step (b).

14. The method of claim 3 wherein the semivolatile species are stripped from said vapor fraction by contacting said vapor fraction with a mass transfer medium.

15. The method of claim 14 wherein the mass transfer medium comprises a solvent selected from the group consisting of benzyl alcohol, propylene carbonate, and gamma butyrolactone.

16. The method of claim 14 wherein the solvent is benzyl alcohol and said mass transfer medium comprises benzyl alcohol.

17. A method of recovering an aromatic alcohol from an effluent comprising at least 10 percent by weight of monomeric units, comprising the steps of:
    (a) polymerizing the monomeric units in the effluent stream under conditions effective to reduce the monomeric units to less than 10 weight percent of the stream;
    (b) feeding the effluent stream to a heat exchanger type evaporator, and separating water and volatiles from the aromatic alcohol to provide a dewatered aromatic alcohol containing liquid; and
    (c) evaporating the dewatered aromatic alcohol containing liquid in an evaporator to separate the aromatic alcohol from non-volatile materials and recovering therefrom a vapor fraction comprising said aromatic alcohol and a sludge fraction containing non-volatile species in the aromatic alcohol.

18. The method of claim 17 further comprising stripping semi-volatile species from the vapor fraction of step (c) to provide a stripped vapor fraction comprising said aromatic alcohol and a liquid fraction comprising said semi-volatile species.

19. The method of claim 17 wherein said aromatic alcohol is benzyl alcohol.

20. The method of claim 18 wherein said aromatic alcohol is benzyl alcohol.

21. The method of claim 19 further comprising separating the stripped vapor fraction in a fractionating unit into a higher vapor pressure fraction comprising benzaldehyde and a lower vapor pressure fraction comprising benzyl alcohol.

22. The method of claim 20 further comprising separating the stripped vapor fraction in a fractionating unit into a higher vapor pressure fraction comprising benzaldehyde and a lower vapor pressure fraction comprising benzyl alcohol.

23. The method of claim 17 further comprising recovering the sludge fraction of step (c) and separating the sludge fraction to recover the aromatic alcohol therefrom and to provide a waste sludge.

24. The method of claim 23 wherein from about 5 ppm to about 500 ppm of a stabilizer is added to the waste sludge.

* * * * *

UNITED STATES PATENT AND TRADEMARK OFFICE
CERTIFICATE OF CORRECTION

PATENT NO. : 6,187,965 B1
DATED : February 13, 2001
INVENTOR(S) : Anilkumar C. Bhatt and Jerome J. Wagner It is certified that error appears in the above-identified patent and that said Letters Patent is hereby corrected as shown below:

<u>Title page, Abstract,</u>
Line 17, after "evaporated" add the following:
-- , for example in a wiped film type evaporator, --.

Signed and Sealed this

Twenty-third Day of October, 2001

Attest:

*Nicholas P. Godici*

NICHOLAS P. GODICI
*Attesting Officer*   *Acting Director of the United States Patent and Trademark Office*